United States Patent [19]
Nair

[11] Patent Number: 5,568,128
[45] Date of Patent: Oct. 22, 1996

[54] SELF LEARNING DIAPER WETNESS DETECTOR AND TOILET TRAINER

[76] Inventor: Rajesh M. Nair, 9 Saxford La., Nashua, N.H. 03063

[21] Appl. No.: 337,879

[22] Filed: Nov. 14, 1994

[51] Int. Cl.[6] .................................................. G08B 21/00
[52] U.S. Cl. .......................... 340/604; 340/573; 128/734; 128/885; 128/886; 604/361
[58] Field of Search ...................................... 340/604, 573; 128/886, 885, 734; 604/361

[56] References Cited

U.S. PATENT DOCUMENTS

| | | | |
|---|---|---|---|
| 3,508,235 | 4/1970 | Baisen | 340/573 |
| 4,106,001 | 8/1978 | Mahoney | 340/604 |
| 4,205,672 | 6/1980 | Dvorak | 340/573 |
| 4,768,023 | 8/1988 | Xie | 340/573 |
| 4,796,014 | 1/1989 | Chia | 340/573 |
| 4,977,906 | 12/1990 | DiScipio | 128/885 |
| 5,036,859 | 8/1991 | Brown | 128/734 |
| 5,264,830 | 11/1993 | Kline et al. | 340/604 |
| 5,266,928 | 11/1993 | Johnson | 340/604 |
| 5,416,469 | 5/1995 | Colling | 340/573 |

*Primary Examiner*—Jeffery Hofsass
*Assistant Examiner*—Benjamin C. Lee
*Attorney, Agent, or Firm*—Iandiorio & Teska

[57] ABSTRACT

Early detection and warning of wetness in a diaper leads to an early change of diapers, keeping the infant dry and healthy. This invention monitors the diaper for dryness by sensing the conductance between two terminals in contact with the diaper. The device aids in toilet training the infant by learning wetting patterns and providing early warning. The device promotes the efficient use of diapers and reduces the cost of using diapers.

5 Claims, 3 Drawing Sheets

SELF LEARNING DIAPER WETNESS DETECTOR AND TOILET TRAINER

BACKGROUND

1. Field of Invention

This invention relates to child-care, specifically to diaper usage and toilet training.

2. Description of Prior Art

Convenience of use, availability and easy disposal are the main factors that promoted the use of disposable diapers. While the advantages of these over cloth diapers are evident, the environmental impact of the growth in use of disposable diapers has been disastrous. Disposable diapers do not disappear when we throw them into a waste basket. The New York Times has named the disposable diapers as the premier "symbol of nation's garbage crisis". In the book Save our Planet Diane MacEachern says that we throw away enough diapers to fill a barge half a city block long every six hours of each day and we all pay an average $350 million annually to get rid of the so called disposable diapers, even if we have no kids. A child can use 8000 to 10000 diapers before becoming fully toilet trained and it takes twenty trees to keep one baby in disposable diapers for two years. About 800 million pounds of paper is used each year to make $3.3 billion worth of throwaway diapers, and no part of it is recyclable. This leads to the wastage of nearly 800,000 tons of plastic and 100,000 tons of paper pulp each year. With such compelling statistics one might think that even a small percentage reduction in use of disposable diapers would make a significant change in the total waste generated. This was one of the driving forces behind this invention.

Health of the baby was another major factor that led to this invention. Any parent who has seen a child suffer from diaper rash knows that it is a vary painful condition. Interestingly, it is also very easy to avoid it. The primary cause of this condition is long contact of the baby's skin with a wet diaper. The chemicals in urine penetrate tiny cracks in the skin surface and cause infection. Though there is medication available to treat this condition, minimization of length of exposure is the most effective way of prevention.

The only way to achieve above the goals of eliminating the use of diapers and keeping the baby dry, is to toilet train the child as early as possible. Toilet training is a difficult and tedious process for both the child and the parents. Making this process easier and faster was the third factor driving this invention.

The two usual methods followed by caregivers to perform diaper change are a) Timed Diaper Change and b) Change When Soiled. The former, as the name suggests, is performed at frequent intervals whether the diaper is soiled or not. The biggest drawback with this method is that since the diaper status is not monitored it could be soiled right after the change and will not be noticed till next change exposing the baby's skin to long hours of contact with urine. Since the diaper is changed whether dry or soiled, the diapers may not be used efficiently. Using each diaper to its limit reduces the number of diapers used, reduces cost of use of diapers and significantly cut down on waste generated.

The second method involves frequent checking of the diaper and changing when necessary. This method provides the most efficient use of diapers and ensures minimal contact of the baby's skin with a soiled diaper. However it is difficult to constantly monitor the diaper when taking care of several babies or when busy with other things. In practice, the caregiver normally performs a combination of the two methods.

Constant monitoring of wetness as a means of detecting soiled diapers can facilitate all of the above mentioned goals: reduction in skin exposure to chemicals, lower cost of use of diapers and lower waste generated. Automating this monitoring process would be ideal as it can save the effort of frequent checking. A product to detect wetness in a diaper has been attempted before. The most common approach has been through measurement of conductance between two locations on the diaper as shown in U.S. Pat. No. 4,205,672 to Karel Dvorak (Jun. 3, 1980), U.S. Pat. No. 4,704,108 to Shigeru Okada & Katsutoshi Rokuta (Nov. 3, 1987), U.S. Pat. No. 4,796,014 to Jack T Chia (Jan. 3, 1989), U.S. Pat. No. 5,264,830 to Michael J Kline, Paul A Pottgen & Nell J Szuminsky (Nov. 23, 1993) and U.S. Pat. No. 5,266,928 to Lonnie Johnson (Nov. 30, 1993).

In Dvorak the invention senses the wetness between a sensing conductor probe that is built into the diaper and the body of the infant. Dvorak requires one conductive pad inside the diaper material extending to the area between the baby's legs. This calls for a special diaper used for wetness sensing only with these detectors. Three drawbacks of this design are that special type of diaper with a conducting layer in the middle is needed for use with this device, one of the electrical terminals directly contact the infant's skin and the visual alarm is of little help when it is under clothing.

Okada et al., require two such conductive layers. The device by Okada et al. requires two conducting layers built into the diaper to operate. The invention senses the conductivity between them and generates an audible alarm. Again a diaper specially designed for this product is required.

Chia uses a safety pin with two conductors wound together as the sensing pick up and to hold the device in place. The safety pin has a unit with electronics to sense conductivity and generate alarm. Since the contacts are very close, chemicals could build up between them and change the isolation resistance between them, leading to faulty detection.

Kline et al., suggest a pair of outer waterproof pants with two terminals that contact the cotton reusable diaper when worn over it. The wetness monitor is snapped on to the terminals. The conductance between the terminals is monitored for wetness determination. The major drawback is that this could be only used with reusable cotton diapers that normally have no plastic outer layer and not with disposable diapers.

Johnson uses an elongated strip with two conductive pads for sensing conductance at an area on the diaper between the legs of the infant. This strip is connected to the monitoring electronics mounted on the diaper. This strip is discarded with each diaper while the electronic module is reused. Though this product can be used on any kind of diapers, a new conductance sensing strip need to be used with each new diaper to use this product. This could cause inconvenience of stocking these strips, the waste generated and higher cost of use of this product.

OBJECTS AND ADVANTAGES

Accordingly, several objects and advantages of my invention are:

To reduce the risk of diaper and other such skin conditions by minimizing the exposure of the infant to moisture.

To help use diapers more efficiently and reduce waste generated and reduce cost of use of diapers.

To help in child care by automating the tedious job of monitoring of the dryness of diaper.

A device that significantly helps in the toilet training process and get the child out of diapers at an earlier age.

A simple and easy to use wetness detector, that can be used with any existing kinds of diapers, without the need for any disposable parts or modifications in the diaper.

Still further objects and advantages will become apparent from a consideration of the ensuing description and accompanying drawings.

Figure 1A:
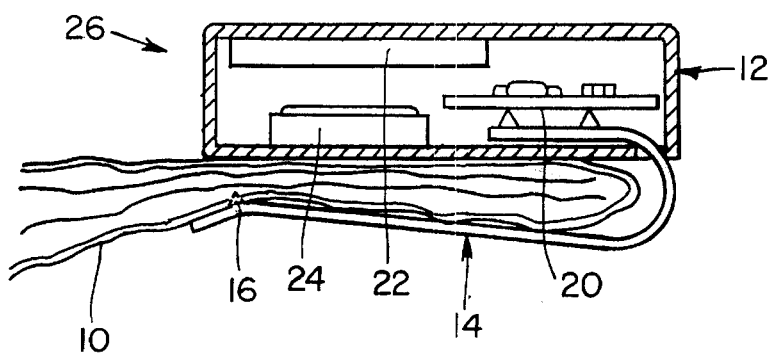
FIG. 1A is a perspective view of my invention used on a diaper showing the clip that acts as terminals and the enclosure for electronics.

REFERENCE NUMERALS 10 diaper
12 enclosure
14 clips
16 terminals
18 insulated coating
20 circuit board
22 speaker
24 battery
26 sensing member
28 microcontroller
30 contacts
32 reference resistor
34 capacitor
36 sockets
38 spikes
40 band
42 straps
44 loops
46 metal contacts
48 time line
50 event markers
52 event time
54 event probability

SUMMARY

A diaper wetness detector, that can be used with any presently available diaper, is described here. This device saves the cam giver from constantly monitoring the diaper for wetness, reduces risk of diaper rash on the infant and enable efficient use of each diaper leading to reduced cost and wastage. The device could also be equipped with a feature to learn the wetting pattern of the infant to assist in toilet training of the infant.

PREFERRED EMBODIMENT

Description

Figure 1B:
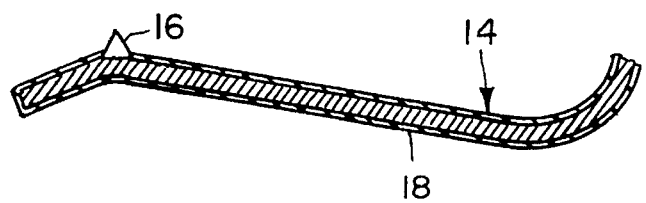
FIG. 1B is a view of the clip and the conductance sensing terminals.

As shown in FIG. 1A the sensing member is plugged on a diaper 10. The sensing member consists of two main parts the enclosure 12 containing the electronics and the clips 14. The clips 14 are made of tensile material and have at the end projections that act as terminals 16 to sense conductance. FIG. 1B shows the clips 14 that have insulated coating 18 in areas to keep them electrically isolated from the infant's body and to give a smoother and softer finish. The terminals 16 are left exposed. FIG. 1A also shows the enclosure 12 that contains the circuit board 20 carrying the electronic components, the speaker 22 and the battery 24. The clips 14 make contact with the circuit board 20 inside the enclosure 12 enabling the circuit to make conductance measurement on the diaper 10.

Figure 2A:
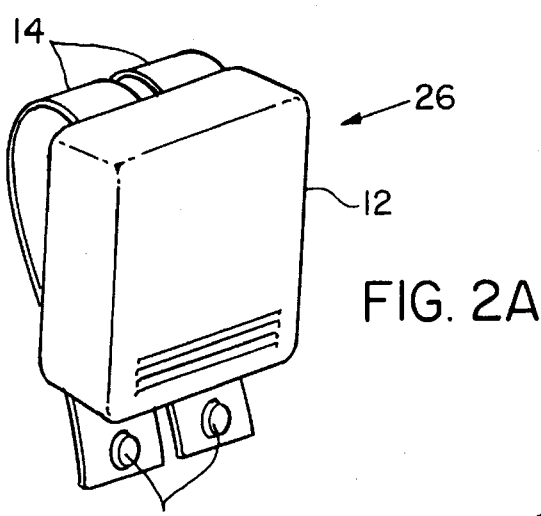
FIG. 2A is a three dimensional view of the diaper wetness detector of the present invention.
Figure 2B:
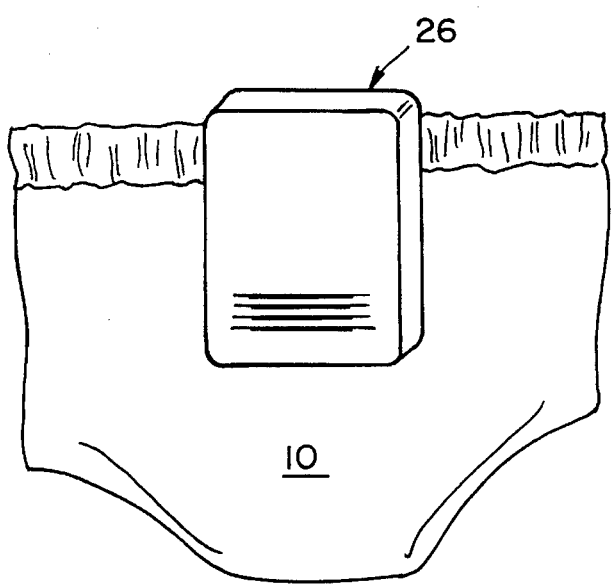
FIG. 2B is a front view showing the diaper wetness detector attached to a diaper for use in accordance with the preset invention.

FIG. 2A shows sensing member 26 including enclosure 12 and clips 14. FIG. 2B shows how sensing member 26 is used on diaper 10. The sensing member 26 is worn on the front of the diaper. Since the abdominal area is soft, the discomfort caused is minimal. The enclosure 12 stays outside the diaper and the clips 14 go inside. The clips 14 reach into the diaper to sense conductance. When the diaper is wet, the bottom part will be more moist than the top. But the device is designed to sense lower moisture at the top of the diaper to detect larger moisture at the bottom.

Figure 3:
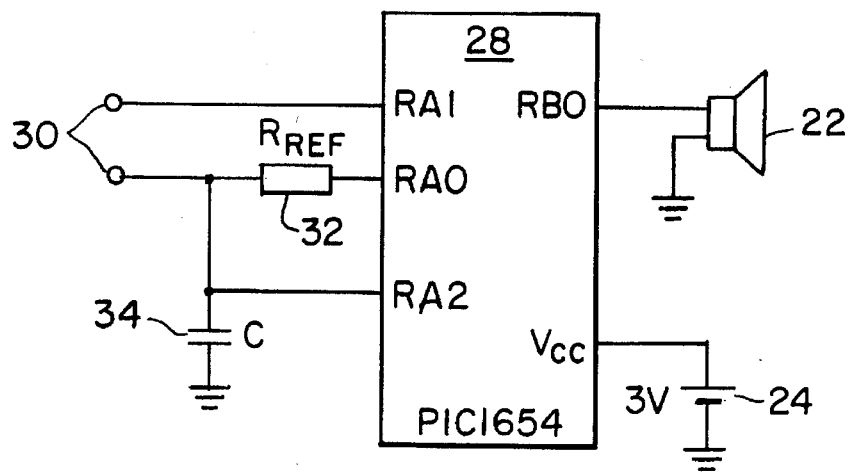
FIG. 3 shows the electronic circuit diagram showing the microcontroller, battery, the speaker and the conductance sensing means.

The electronic circuit as shown in FIG. 3 consists of a microcontroller 28 that is powered by a battery 24. A speaker 22 is connected to the microcontroller 28 for generation of audible alarm. The terminals 16 on the clips 14 are connected to the contacts 30 in the circuit. The capacitor 34 is connected to the reference resistor 32, the sensing contacts 30 and the microcontroller 28.

Operation

When the sensing member 26 is worn on a diaper 10 as shown in FIG. 1A, the terminals 16 at the end of the clips 14 make contact with the inside of the diaper 10. The wetness of the diaper is determined by measuring the resistance offered by the moisture between the two terminals 16 as shown in FIG. 1A.

The resistance between the terminals 16 is measured as shown in the circuit diagram FIG. 3. The capacitor 34 is charged through the reference resistor 32 by applying a voltage across the reference resistor 32. The time taken to charge the capacitor 34 is measured through a timer counter in the microcontroller 28. The process is repeated and same capacitor 34 is now charged through the resistance across the terminals 16. The charging time is measured by the microcontroller 28. If the charging time for the test resistance between the contact is shorter than that for the reference resistor, the diaper is considered wet. When the diaper is found wet, the microcontroller 28 generates chimes through the speaker 22.

Figure 6:
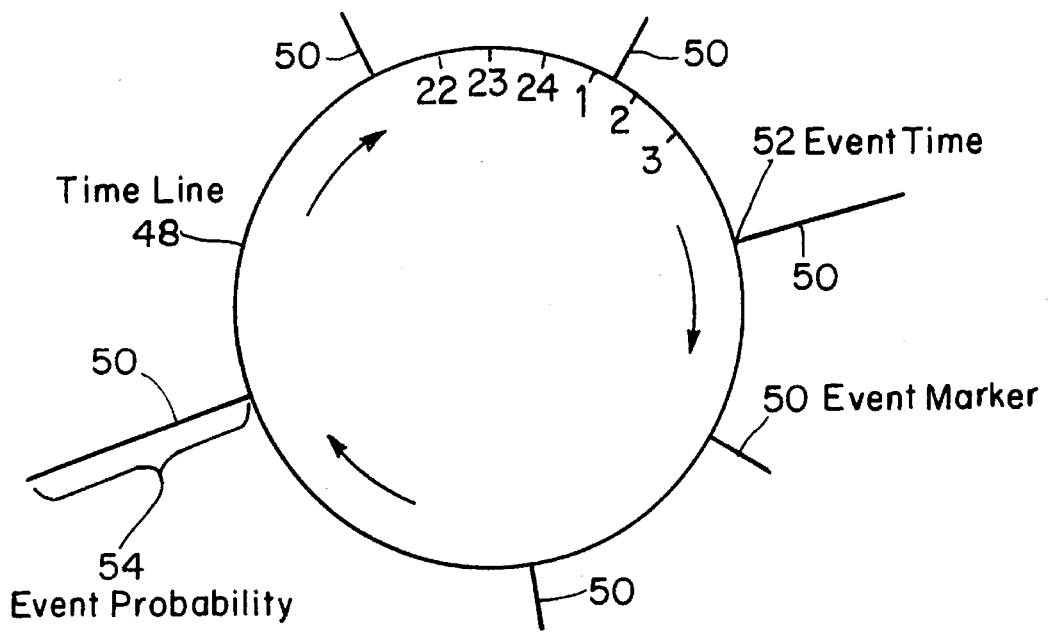
FIG. 6 shows the time chart used for learning of the wetness pattern.

An algorithm in the program that runs in microcontroller 28 learns the wetting pattern of the infant. This information is then used early warning to take the infant to the toilet. The learning algorithm uses a twenty-four hour clock to time wetting events. The microcontroller 28 has a timer counter that acts as this clock. On a time chart as shown in the FIG. 6, the time line 48 is represented by a closed loop counter. Each time instant where wetting could happen is represented by an event marker 50. There are six event markers 50 that represent locations of maximum likelihood of wetting on the time line 48. Each event marker 50 has an event time 52 that shows the time instant of wetting and an event probability 54 that shows the likelihood of wetting happening. Both event time 52 and event probability 54 are updated each day. If a wetting happens at or near the event time 52, the event probability 54 is incremented and the event time 52 is modified. If a wetting does not occur, the event probability 54 is decremented. Therefore the sensing member can learn and unlearn wetting pattern with time. If an event probability 54 is higher than a set value, the event is tagged as a probable event. When the time counter is a few minutes before reaching a probable event, a warning alarm is generated to take the child to the toilet.

OTHER EMBODIMENTS

Second design

Description

Figure 4A:
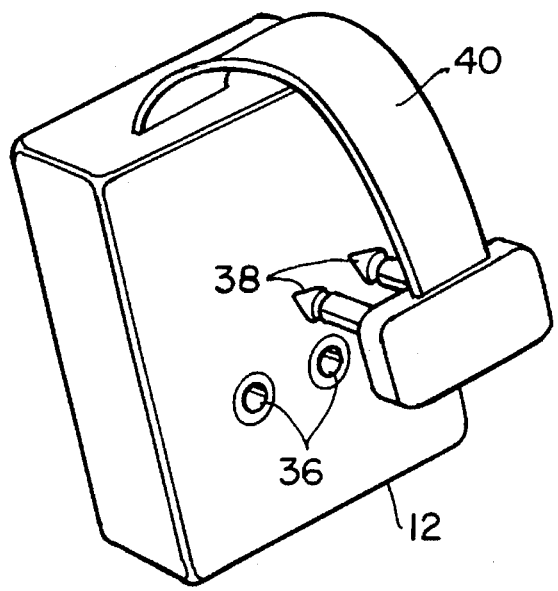
FIG. 4 is a different design of the invention that uses two spikes to fasten and sense moisture.
Figure 4B:
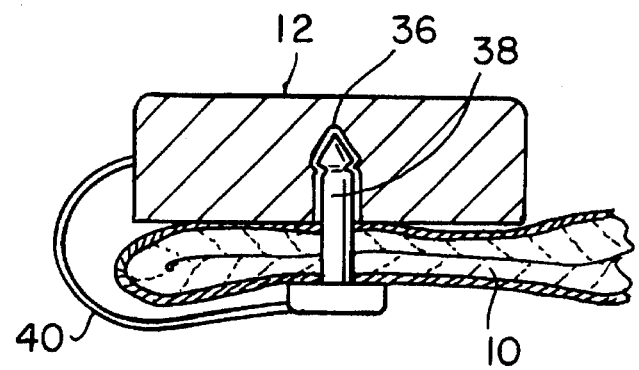

A second design for the product is shown in the FIG. 4. Here the clips 14 and the terminals 16 in FIG. 1 are replaced with two sockets 36 and spikes 38. The spikes 38 poke through the diaper 10 and lock into the sockets 36. A band 40 helps in positioning the spikes 38 while putting on. As in the previous case the enclosure 12 stays outside the diaper. The conductance between the spikes 38 is sensed to determine wetness. The tensile band 40 is designed such that the spikes 38 and the sockets 36 are together and it takes force to part them. This guarantees that the spikes 38 are not exposed normally.

Operation

The operation of the second design is different from the first only in its mounting method. As in FIG. 4 the enclosure 12 contains two sockets 36 that accepts the spikes 38 at the end of the tensile band 40. The spikes 38 poke through the diaper 10 and seats in side the sockets 36. The sockets 36 are connected to the circuit board in the enclosure 12. The microcontroller in the enclosure senses the conductance between the spikes and determines if the diaper is wet.

Third Design

Description

Figure 5:
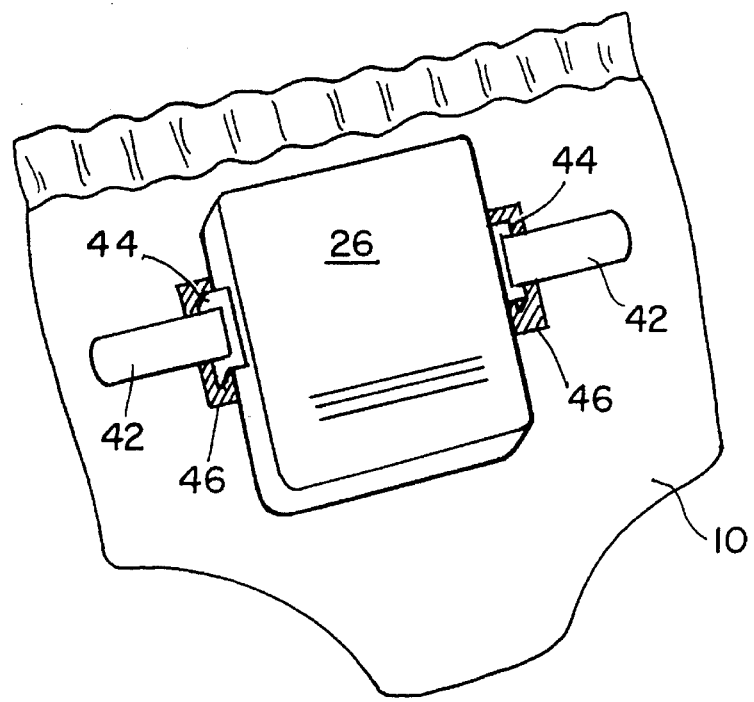
FIG. 5 shows a modified version that is used with a specially designed diaper.

A third design of the product is shown in FIG. 5. Here certain features are built into the diaper for proprietary use of the device on certain kind of diapers. The diaper will have two peelable straps 42. These straps 42 are passed through the metal loops 44 on the device and stuck back on the diaper as shown in FIG. 5. The loops 44 also act as terminals for sensing conductance between the two metal contacts 46 on the diaper.

Operation

As shown in FIG. 5 the device is placed such that the metal loops 44 make contact with the metal contacts 46 on the diaper and the straps 42 are fastened. The loops 44 are in contact with the circuit board 20 inside the enclosure 12 thereby enabling the microcontroller 28 to sense the conductance between the metal contacts 46 on the diaper. The operation of the product is the same as the other two designs. After use of each diaper, the device is removed and used on the next one.

CONCLUSION, RAMIFICATIONS, AND SCOPE

Accordingly, it can be seen that the use of the device can achieve the following important effects:
1. Significantly reduce the risk of skin conditions such as diaper rash on an infant and keep the infant dry and healthy.
2. Improve the efficiency of use of each diaper, leading to significant reduction in the number of diapers used and money spent on diapers.
3. Reduction in waste generated. Considering disposable diapers make a significant portion of non-biodegradable waste, any reduction in the number of diapers used can have a positive environmental effect.
4. Help toilet train the child at an early age leading to achievement of all of the above effects as early as possible.

Though the operation of the device can be the same, several physical designs that are adapted for different types of uses are possible.

Although the description above contains many specificities, these should not be construed as limiting the scope of the invention but as merely providing illustrations of some of the presently preferred embodiments of this invention. Various other embodiments and ramifications are possible within its scope. For example, the same device can be used in other similar applications such as for aged and critical care patients with reduced bladder control.

Thus the scope of the invention should be determined by the appended claims and their legal equivalents, rather than by the examples given.

I claim:
1. A wetness detector comprising:

a housing;

a biased attachment clip for attaching said housing to the outside of an undergarment proximate the waist band of the undergarment, said biased attachment clip extending over the waist band, a terminal end of said biased attachment clip extending inside the undergarment;

a pair of spaced electrodes affixed directly on the terminal end of said biased attachment clip and directed towards the housing so that said clip functions both as an attachment means for attaching the housing to the outside of the undergarment and as the electrodes thereby eliminating the need for additional electrodes; and means, located within the housing and connected to said electrodes, for sensing wetness of said undergarment.

2. The wetness detector of claim 1 in which said terminals have sharpened ends for piercing the undergarment, said housing includes receptacles for receiving said terminals.

3. A self learning wetness detector and trainer system comprising:

a housing;

a biased attachment clip for attaching said housing to an undergarment;

a pair of spaced electrodes affixed to directly to said attachment clip and directed towards the housing for detecting wetness of the undergarment;

said housing including;

a timer;

storage means, responsive to said electrodes and said timer, for storing the time of an occurrence of a detected wetness event;

means, responsive to said storage means and said electrode, for assigning a wetness probability to each said stored wetness event, said means for assigning including;

means for automatically increasing the wetness probability of a stored prior wetness event in response to a subsequent wetness event detected proximate the time stored for the stored prior wetness event, and means for automatically decreasing the wetness probability of a stored prior wetness event in response to a lack of subsequent wetness events detected proximate the time stored for the stored prior wetness event;

means for storing a wetness event probability threshold; an alarm and means, responsive to said stored threshold, for energizing said alarm proximate the stored time of a wetness event having a wetness probability greater than said threshold.

4. The system of claim 3 further including means for adjusting the time of a stored prior wetness event in response to a subsequent wetness event time proximate but different than the stored prior wetness event time.

5. A wetness detector comprising;

a housing;

an attachment clip for attaching said housing to the outside of an undergarment proximate the waist band of the undergarment, said attachment clip extending over the waist band, a terminal end of said attachment clip extending inside the undergarment;

a pair of spaced electrodes affixed directly on the terminal end of said attachment clip and directed towards the housing;

detection means, located within the housing and connected to said electrodes, for sensing wetness of said undergarment;

said housing including;

a timer;

storage means, responsive to said detection means and said timer, for storing the time of an occurrence of a detected wetness event;

means, responsive to said storage means and said detection means, for assigning a wetness probability to each said storage wetness event, said means for assigning including:

means for automatically increasing the wetness probability of a stored prior wetness event in response to a subsequent wetness event detected proximate the time stored for the stored prior wetness event, and means for automatically decreasing the wetness probability of a stored prior wetness event in responsive to a lack of subsequent wetness events detected proximate the time stored for the stored prior wetness event;

means for storing a wetness event probability threshold;

an alarm; and means, responsive to said stored threshold, for energizing said alarm proximate the stored time of a wetness event having a wetness probability greater than said threshold.

\* \* \* \* \*